United States Patent
Hartley

(10) Patent No.: US 6,518,026 B2
(45) Date of Patent: *Feb. 11, 2003

(54) PROCESS FOR CONTROLLING CONTAMINATION OF NUCLEIC ACID AMPLIFICATION REACTIONS

(75) Inventor: James L. Hartley, Frederick, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/782,516

(22) Filed: Feb. 14, 2001

(65) Prior Publication Data

US 2002/0072095 A1 Jun. 13, 2002

Related U.S. Application Data

(63) Continuation of application No. 09/344,491, filed on Jun. 25, 1999, now Pat. No. 6,287,823, which is a continuation of application No. 08/962,701, filed on Nov. 3, 1997, now Pat. No. 5,945,313, which is a continuation of application No. 08/221,465, filed on Apr. 1, 1994, now Pat. No. 5,683,896, which is a continuation of application No. 08/079,835, filed on Jun. 22, 1993, now abandoned, which is a continuation of application No. 07/728,874, filed on Jul. 12, 1991, now abandoned, which is a continuation-in-part of application No. 07/633,389, filed on Dec. 31, 1990, now abandoned, which is a continuation-in-part of application No. 07/401,840, filed on Sep. 1, 1989, now abandoned, and a continuation-in-part of application No. 07/360,120, filed on Jun. 1, 1989, now Pat. No. 5,035,996.

(51) Int. Cl.$^7$ ............... C12Q 1/68; C12P 19/34; C07H 21/04; C07H 21/02

(52) U.S. Cl. ............... 435/6; 435/91.2; 435/196; 536/24.33; 536/221

(58) Field of Search ............... 435/6, 91.2, 810, 435/196; 536/24.33, 22.1

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,873,192 A | 10/1989 | Kunkel | 435/172.3 |
| 4,876,187 A | 10/1989 | Duck et al. | 435/6 |
| 4,965,188 A | 10/1990 | Mullis et al. | 435/6 |
| 5,035,996 A | 7/1991 | Hartley | 435/6 |
| 5,137,814 A | 8/1992 | Rashtchian et al. | 435/91 |
| 5,310,652 A * | 5/1994 | Gelfand et al. | 435/6 |
| 5,334,515 A | 8/1994 | Rashtchian et al. | 435/91.2 |
| 5,418,149 A | 5/1995 | Gelfand et al. | 435/91.2 |
| 5,427,929 A | 6/1995 | Richards et al. | 435/91.2 |
| 5,683,896 A | 11/1997 | Hartley et al. | 435/91.1 |
| 5,945,313 A | 8/1999 | Hartley et al. | 435/91.2 |
| 6,287,823 B1 * | 9/2001 | Hartley | 435/91.2 |

FOREIGN PATENT DOCUMENTS

| | | |
|---|---|---|
| EP | 0 123 513 B1 | 10/1984 |
| EP | 0 200 362 B1 | 12/1986 |
| EP | 0 237 362 B2 | 9/1987 |
| EP | 0 258 017 B1 | 3/1988 |
| EP | 0 320 308 B1 | 6/1989 |
| EP | 0 336 731 B1 | 10/1989 |
| EP | 0 401 037 B1 | 12/1990 |
| EP | 0 407 291 A1 | 1/1991 |
| EP | 0 415 755 B1 | 3/1991 |
| EP | 0 415 755 A3 | 8/1991 |
| EP | 0 401 037 A3 | 9/1991 |
| WO | WO 88/10315 | 12/1988 |
| WO | WO 89/09835 | 10/1989 |
| WO | WO 89/11548 | 11/1989 |
| WO | WO 91/00363 | 1/1991 |
| WO | WO 91/17270 | 11/1991 |

OTHER PUBLICATIONS

Almoguera, C. et al., "Most Human Carcinomas of the Exocrine Pancreas Contain Mutant c–K–ras Genes," *Cell* 53:549–554, Cell Press (May 1988).

Barany, F., "Genetic disease detection and DNA amplification using cloned thermostable ligase," *Proc. Natl. Acad. Sci. USA* 88:189–193, The National Academy of Sciences of the USA (Jan. 1991).

Bos, J.L. et al., "Prevalence of ras gene mutations in human colorectal cancers," *Nature* 327:293–297, Macmillan Magazines Ltd (1987).

Cimino, G.D. et al., "More false–positive problems," *Nature* 345:773–774, Macmillan Magazines Ltd (Jun. 1990).

Delort, A.–M. et al., "Excision of uracil residues in DNA: mechanism of action of *Escherichia coli* and *Micrococcus luteus* uracil–DNA glycosylases," *Nucleic Acids Res.* 13:319–335, IRL Press (1985).

Doetsch, P.W., and Cunningham, R.P., "The enzymology of apurinic/apyrimidinic endonucleases," *Mutation Res.* 236:173–201, Elsevier Science Publishers B.V. (Sep. 1990).

(List continued on next page.)

*Primary Examiner*—Stephanie W. Zitomer
(74) *Attorney, Agent, or Firm*—Sterne, Kessler, Goldstein & Fox P.L.L.C.

(57) ABSTRACT

This invention relates to a method of incorporating an exo-sample nucleotide into the amplified product strands resulting from a nucleic acid amplification process. Once the product strands have been obtained and analyzed (e.g., by hybridization, Southern blot, etc.), the exo-sample strands can be selectively destroyed by acting on the incorporated exo-sample nucleotide.

Two embodiments are presented. In a first embodiment, the exo-sample nucleotide is incorporated by carrying out the amplification reaction in the presence of an excess of exo-sample nucleotide triphosphate.

In a second embodiment, the exo-sample nucleotide is incorporated by carrying out the amplification reaction in the presence of an oligonucleotide which has, as part of its sequence, one or more exo-sample nucleotides.

72 Claims, 1 Drawing Sheet

OTHER PUBLICATIONS

Duncan, B.K., "DNA Glycosylases," in *The Enzymes, vol. XIV, Nucleic Acids, Part A*, Boyer, P.D., ed., 3$^{rd}$ edition, Academic Press, Inc., New York, NY, pp. 565–586 (1981).

Engelke, D.R. et al., "Direct sequencing of enzymatically amplified human genomic DNA," *Proc. Natl. Acad. Sci. USA 85*:544–548, The National Academy of Sciences of the USA (Jan. 1988).

Erlich, H.A. et al., "Specific DNA amplification," *Nature 331*:461–462, Macmillan Magazines Ltd (Feb. 1988).

Farr, C.J. et al., "Analysis of RAS gene mutations in acute myeloid leukemia by polymerase chain reaction and oligonucleotide probes," *Proc. Natl. Acad. Sci. USA 85*:1629–1633, The National Academy of Sciences of the USA (Mar. 1988).

Higuchi, R. et al., "DNA typing from single hairs," *Nature 332*:543–546, Macmillan Magazines Ltd (Apr. 1988).

Higuchi, R. et al., "A general method of in vitro preparation and specific mutagenesis of DNA fragments: study of protein and DNA interactions," *Nucleic Acids Res. 16*:7351–7367, IRL Press (Aug. 1988).

Kornberg, A. and Baker, T.A., in *DNA Replication*, 2$^{nd}$ Edition, W.H. Freeman and Company, New York, NY, pp. 136–137 (1992).

Kwoh, D.Y. et al., "Transcription–based amplification system and detection of amplified human immunodeficiency virus type 1 with a bead–based sandwich hybridization format," *Proc. Natl. Acad. Sci. USA 86*:1173–1177, The National Academy of Sciences of the USA (Feb. 1989).

Kwok, S. et al., "Identification of Human Immunodeficiency Virus Sequences by Using In Vitro Enzymatic Amplification and Oligomer Cleavage Detection," *J. Virol. 61*:1690–1694, American Society for Microbiology (1987).

Kwok, S. and Higuchi, R., "Avoiding false positives with PCR," *Nature 339*:237–238, Macmillan Magazines Ltd (May 1989).

Langer, P.R. et al., "Enzymatic synthesis of biotin–labeled polynucleotides: Novel nucleic acid affinity probes," *Proc. Natl. Acad. Sci. USA 78*:6633–6637, The National Academy of Sciences of the USA (1981).

Li, H. et al., "Amplification and analysis of DNA sequences in single human sperm and diploid cells," *Nature 335*:414–417, Macmillan Magazines Ltd (Sep. 1988).

Lindahl, T. et al., "DNA N–Glycosidase. Properties of Uracil–DNA Glycosidase from *Escherichia coli*," *J. Biol. Chem. 252*:3286–3294, The American Society of Biological Chemists, Inc. (1977).

Loh, E.Y. et al., "Polymerase Chain Reaction with Single–Sided Specificity: Analysis of T Cell Receptor δ Chain," *Science 243*:217–220, American Association for the Advancement of Science (Jan. 1989).

Longo, M.C. et al., "Use of uracil DNA glycosylase to control carry–over contamination in polymerase chain reactions," *Gene 93*:125–128, Elsevier Science Publishers B.V. (Sep. 1990).

Marx, J.L., "Multiplying Genes by Leaps and Bounds," *Science 240*:1408–1410, American Association for the Advancement of Science (Jun. 1988).

Maxam, A.M. and Gilbert, W., "A new method for sequencing DNA," *Proc. Natl. Acad. Sci. USA 74*:560–564, The National Academy of Sciences of the USA (1977).

Mole, S.E. et al., "Using the polymerase chain reaction to modify expression plasmids for epitope mapping," *Nucleic Acids Res. 17*:3319, IRL Press (Apr. 1989).

Mullis, K. et al., "Specific Enzymatic Amplification of DNA In Vitro: The Polymerase Chain Reaction," *Cold Spring Harb. Symp. Quant. Biol. 51*:263–273, Cold Spring Harbor Laboratory Press (1986).

Mullis, K.B. and Faloona, F.A., "Specific Synthesis of DNA in Vitro via a Polymerase–Catalyzed Chain Reaction," *Methods Enzymol. 155*:335–350, Academic Press (1987).

Orlandi, R. et al., "Cloning immunoglobulin variable domains for expression by the polymerase chain reaction," *Proc. Natl. Acad. Sci. USA 86*:3833–3837, The National Academy of Sciences of the USA (May 1989).

Oste, C., "Polymerase Chain Reaction," *BioTechniques 6*:162–167, Eaton Publishing Co (Feb. 1988).

Ou, C.–Y. et al., "DNA Amplification for Direct Detection of HIV–1 in DNA of Peripheral Blood Mononuclear Cells," *Science 239*:295–297, American Association for the Advancement of Science (Jan. 1988).

Perkin–Elmer Corporation, "GeneAmp® PCR Carry–over Prevention Kit," in: *PE Express*, B–3, p. 2 (1990).

Saiki, R.K. et al., "Enzymatic Amplification of β–Globin Genomic Sequences and Restriction Site Analysis for Diagnosis of Sickle Cell Anemia," *Science 230*:1350–1354, American Association for the Advancement of Science (1985).

Saiki, R.K. et al., "Primer–Directed Enzymatic Amplification of DNA with a Thermostable DNA Polymerase," *Science 239*:487–491, American Association for the Advancement of Science (Jan. 1988).

Schaaper, R.M. et al., "Infidelity of DNA synthesis association with bypass of apurinic sites," *Proc. Natl. Acad. Sci. USA 80*:487–491, The National Academy of Sciences of the USA (1983).

Syvänen, A.–C. et al., "Quantification of polymerase chain reaction products by affinity–based hybrid collection," *Nucleic Acids Res. 16*:11327–11338, IRL Press (Dec. 1988).

Varshney, U. and van de Sande, J.H., "Specificities and Kinetics of Uracil Excisions from Uracil–Containing DNA Oligomers by *Escherichia coli* Uracil DNA Glycosylase," *Biochemistry 30*:4055–4061, The American Chemical Society (Apr. 1991).

Vosberg, H.–P., "The polymerase chain reaction: an improved method for the analysis of nucleic acids," *Hum. Genet. 83*:1–15, Springer–Verlag (Aug. 1989).

Wong, C. et al., "Characterization of β–thalassaemia mutations using direct genomic sequencing of amplified single copy DNA," *Nature 330*:384–386, Macmillan Magazines Ltd (1987).

Wu, D.Y. and Wallace, R.B., "The Ligation Amplification Reaction (LAR)–Amplification of Specific DNA Sequences Using Sequential Rounds of Template–Dependent Ligation," *Genomics 4*:560–569, Academic Press (May 1989).

Dialog File No. 351, Derwent WPI, English abstract of EP 0 407 291 A1 (document AL3), WPI Accession No. 1991–010244/199102.

\* cited by examiner

PROCESS FOR CONTROLLING CONTAMINATION OF NUCLEIC ACID AMPLIFICATION REACTIONS

CROSS-REFERENCE TO RELATED APPLICATIONS

This application is a continuation of U.S. application Ser. No. 09/344,491, filed Jun. 25, 1999 (U.S. Pat. No. 6,287, 823), which is a continuation of U.S. application Ser. No. 08/962,701, filed Nov. 3, 1997 (U.S. Pat. No. 5,945,313), which is a continuation of U.S. application Ser. No. 08/221, 465, filed Apr. 1, 1994 (U.S. Pat. No. 5,683,896), which is a continuation of U.S. application Ser. No. 08/079,835, filed Jun. 22, 1993, now abandoned, which is a continuation of U.S. application Ser. No. 07/728,874, filed Jul. 12, 1991, now abandoned, which is a continuation-in-part of U.S. application Ser. No. 07/633,389, filed Dec. 31, 1990, now abandoned, which is a continuation-in-part of U.S. application Ser. No. 07/360,120, filed Jun. 1, 1989 (U.S. Pat. No. 5,035,996), and Ser. No. 07/401,840, filed Sep. 1, 1989, now abandoned. The entire contents of these applications are herein incorporated by reference.

BACKGROUND OF THE INVENTION

1. Field of the Invention

The present invention relates to an improvement in processes which amplify nucleic acid sequences. In particular, invention is directed to a means for eliminating the products of an execution of a nucleic acid amplification process that contaminate subsequent executions of the amplification process.

One embodiment is directed to a method for preventing carryover-contamination of nucleic acid samples by eliminating the products of an execution of an oligonucleotide-dependent nucleic acid amplification process that contaminate subsequent executions of the amplification process. Such oligonucleotide-dependent nucleic acid amplification processes may include, for example, Polymerase Chain Reaction (PCR) and Ligase Chain Reaction (LCR).

The improvements of the present invention ensure that the results of an amplification process do not reflect the presence of carryover-contaminating nucleic acid template.

2. Background Art

The polymerase chain reaction (PCR) procedure amplifies specific nucleic acid sequences through a series of manipulations including denaturation, annealing of oligonucleotide primers, and extension of the primers with DNA polymerase (Mullis, K. B. et al., U.S. Pat. Nos. 4,683,202, 4,683,195; Mullis, K. B., EP 201,184; Erlich, H., EP50,424, EP 84,796; EP 258,017, EP 237,362; Erlich, H., U.S. Pat. No. 4,582, 788; Saiki, R. et al., U.S. Pat. No. 4,683,202; Mullis, K. B. et al. Cold Spring Harbor *Symp. Quant. Biol.* 51:263 (1986); Saiki, R. et al. *Science* 230:1350 (1985); Saiki, R. et al. *Science* 231:487 (1988); Loh, E. Y. et al. *Science* 243:217 (1988)). These steps can be repeated many times, potentially resulting in large amplification of the number of copies of the original specific sequence. It has been shown that even a single copy of a DNA sequence can be amplified to produce hundreds of nanograms of product (Li, H. et al. *Nature* 335:414 (1988)).

Other known nucleic acid amplification procedures include transcription-based amplification systems (Kwoh, D. et al. *Proc. Natl. Acad. Sci. USA* 86:1173 (1989); Gingeras, T. R. et al., WO 88/10315).

Schemes based on ligation of two (or more) oligonucleotides in the presence of a nucleic acid target having the sequence of the resulting "di-oligonucleotide," thereby amplifying the di-oligonucleotide, are also known (Wu, D. Y. and Wallace, R. B. *Genomics* 4:560 (1989); Backman et al., EP 320,308; Wallace, B., EP 336,731; and Orgel. L., WO 89/09835). Such oligonucleotide-dependent amplifications are termed "Ligase Chain Reaction" (LCR).

A consequence of amplification processes, such as PCR or LCR, is that the amplification products themselves can be substrates for subsequent PCR or LCR procedures. Furthermore, because the quantities of the amplification products can be large, and because the sensitivity of PCR and LCR is so great, the dispersal of even an extremely small fraction of a reaction, such as a PCR or LCR reaction, into the laboratory area potentially can lead to contamination of later attempts to amplify other samples, thereby resulting in false positives. Extreme care must be taken to avoid carryover contamination (Kwok, S. and Higuchi, R. *Nature* 339:237 (1989)); this is very inconvenient and adds significantly to the cost of doing amplifications such as PCR and LCR.

Thus a need exists for a routine, economical method of nucleic acid amplification wherein such amplification may be performed without concern as to possible carryover-contamination from previous amplifications.

The invention represents an improvement upon in vitro nucleic acid amplification procedures in general by making amplification products distinguishable from naturally occurring DNA. Accordingly, such products are rendered inactive as templates for further amplification prior to the start of the succeeding amplification reaction.

BRIEF SUMMARY OF THE INVENTION

This invention relates to a method of incorporating an exo-sample nucleotide into the amplified product strands resulting from a nucleic acid amplification process. Once the product strands have been obtained and analyzed (e.g., by hybridization, Southern blot, etc.), the exo-sample strands can be selectively destroyed by acting on the incorporated exo-sample nucleotide.

Two embodiments are presented. In a first embodiment, the exo-sample nucleotide is incorporated by carrying out the amplification reaction in the presence of an excess of exo-sample nucleotide triphosphate.

In a second embodiment, the exo-sample nucleotide is incorporated by carrying out the amplification reaction in the presence of an oligonucleotide which has, as part of its sequence, one or more exo-sample nucleotides. The primer containing exo-sample nucleotide(s) can be used alone or in combination with the first embodiment, i.e., also incorporating the exo-sample nucleotide by carrying out the amplification reaction in the presence of an excess of exo-sample nucleotide triphosphate.

In a variation of the second embodiment, the exo-sample nucleotide is incorporated in at least one oligonucleotide before the amplification reaction. Preferably the exo-sample nucleotide is incorporated at or near the oligonucleotide termini. Before amplification, the oligonucleotide containing exo-sample nucleotide is substantially amplifiable. After amplification, the amplified oligonucleotide (containing exo-sample nucleotide) is substantially unamplifiable. The oligonucleotide containing exo-sample nucleotide may be made unamplifiable by a treatment during the amplification process. Causing the amplified oligonucleotide containing exo-sample nucleotide to be cleaved at or near the location of the exo-sample nucleotide is one example of making such an oligonucleotide substantially unamplifiable.

The invention eliminates the products of previous amplifications from further amplification by means of a treatment that leaves nucleic acid from the sample unaffected in its ability to be amplified. This treatment greatly reduces a major problem associated with amplification of nucleic acids, namely contamination of starting materials with the end products of previous amplification processes. In other words, this invention provides a process of discriminating against amplification products, and in favor of nucleic acids normally found in nature, prior to the start of succeeding amplification reactions.

More specifically, this invention relates to in vitro procedures which utilize enzymes to amplify specific nucleic acid sequences. Examples of such procedures include polymerase chain reaction (PCR) and ligase chain reaction (LCR). A serious limitation of the PCR procedure, the LCR procedure and other similar procedures is contamination of the laboratory environment with the amplified nucleic acid end products of individual reactions. Such contamination commonly results in amplification not only of authentic nucleic acid which may be present in the sample of interest, but also of the contaminating end products from previous reactions. This invention provides a process to remove possible contamination of this type, without affecting the desired amplification of authentic nucleic acids.

The first embodiment involves first performing amplification procedures in which one or more of the four normal ribonucleoside triphosphates (rNTPs) or deoxyribonucleoside triphosphates (dNTPs) is replaced with one or more exo-sample nucleotides that are normally absent from or present very rarely in nucleic acids found in the samples whose amplification is desired. The DNA or RNA produced during such amplification processes can be differentiated from sample nucleic acids. Thus, one can discriminate against nucleic acids produced during amplification processes in favor of sample DNA or RNA prior to or during succeeding amplification processes, such that previously amplified nucleic acid can no longer be amplified, while sample DNA or RNA remains amplifiable.

The present invention represents an improvement upon in vitro oligonucleotide-dependent, nucleic acid amplification procedures. In the methods of the present invention, amplification products are made distinguishable from the nucleic acid substrate used to initiate the amplification in a manner which imparts distinct properties to the amplification products. Accordingly, prior to the start of a new amplification reaction, these distinct properties may be exploited so as to render former amplification products inactive as templates in subsequent amplification reactions.

Therefore, the present invention is directed to:
a process for oligonucleotide-dependent amplification of one or more nucleic acid sequences in a sample, comprising the steps of:
(a) amplifying nucleic acid of a first sample, wherein said amplifying is dependent on one or more specific oligonucleotides, and wherein at least one of such specific oligonucleotides comprises an exo-sample nucleotide, thereby producing amplified nucleic acid containing an exo-sample nucleotide, and
(b) subjecting the nucleic acid of a second sample to treatment which renders said amplified nucleic acid containing an exo-sample nucleotide substantially unamplifiable in an amplification dependent on such specific oligonucleotides and which does not substantially affect amplification of nucleic acid that does not contain the exo-sample nucleotide;
whereby amplified nucleic acid sequences derived from such first sample which contaminate such second sample are not further substantially amplified during amplification dependent on such specific oligonucleotides of the nucleic acid sequences of such second sample.

The present invention is further directed to a process for oligonucleotide-dependent amplification of one or more nucleic acid sequences in a sample, comprising the steps of:
(a) amplifying nucleic acid of a first sample, wherein such amplifying is dependent on one or more specific oligonucleotides, and wherein at least one of said specific oligonucleotides comprises an exo-sample nucleotide, thereby producing amplified nucleic acid containing an exo-sample nucleotide, and
(b) subjecting the nucleic acid of a second sample to treatment which renders said amplified nucleic acid containing an exo-sample nucleotide substantially unamplifiable in an amplification dependent on said specific oligonucleotides and which does not substantially prevent amplification of nucleic acid that does not contain said exo-sample nucleotide;
wherein said oligonucleotide comprising an exo-sample nucleotide before such amplification is substantially less susceptible to said treatment than said amplified nucleic acid containing an exo-sample nucleotide,
whereby amplified nucleic acid sequences derived from said first sample which contaminate said second sample are not further substantially amplified during amplification dependent on said specific oligonucleotides of the nucleic acid sequences of said second sample.

The present invention is further directed to a process for amplifying at least one specific nucleic acid sequence contained in a nucleic acid or a mixture of nucleic acids wherein each nucleic acid consists of two separate complementary strands, of equal or unequal length, which process further comprises:
(e) treating the strands with two oligonucleotide primers, for each different specific sequence being amplified, under conditions such that for each different sequence being amplified an extension product of each primer is synthesized which is complementary to each nucleic acid strand, wherein such primers are selected so as to be sufficiently complementary to different strands of each specific sequence to hybridize therewith such that the extension product synthesized from one primer, when it is separated from its complement, can serve as a template for synthesis of the extension product of the other primer;
(f) separating the primer extension products from the templates on which they were synthesized to produce single-stranded molecules; and
(g) treating the single-stranded molecules generated from step (f) with the primers of step (e) under conditions that a primer extension product is synthesized using each of the single strands produced in step (f) as a template.

Exo-sample nucleotides can, according to the invention, be incorporated during amplification steps (e) and (g) or the exo-sample nucleotide can be incorporated in at least one primer used in step (e) and (g). As will be evident, the exo-sample nucleotide may be incorporated in the amplification product during the amplification steps and as part of the primer. The two oligonucleotide primers of step (e) may or may not be identical.

In addition, the invention is directed to a process for amplifying one or more nucleic acid molecules in a sample, comprising the steps of:

(A) with a first sample containing a nucleic acid sequence or a mixture of nucleic acid molecules, wherein each nucleic acid molecule has two separate complementary strands of equal or unequal length:
  (a) treating such strands with two oligonucleotide primers, for each different specific nucleic acid molecule being amplified, wherein at least one primer comprises an exo-sample nucleotide, under conditions such that for each different nucleic acid molecule being amplified an extension product of each primer is synthesized which is complementary to each nucleic acid strand, wherein such primers are selected so as to be sufficiently complementary to different strands of each specific nucleic acid molecule to hybridize therewith such that the extension product synthesized from one primer, when it is separated from its complement, can serve as a template for synthesis of the extension product of the other primer;
  (b) separating the primer extension products from the nucleic acid molecule templates on which they were synthesized to produce single-stranded molecules;
  (c) treating such single-stranded molecules generated from step (b) with the primers of step (a) under conditions such that a primer extension product is synthesized using each of the single strands produced in step (b) as a template;
  (d) repeating steps (a) through (c) at least once, thereby amplifying the specific nucleic acid sequence contained by such first sample; and
(B) with a second sample containing a nucleic acid molecule or a mixture of nucleic acid molecules, wherein each nucleic acid molecule has two separate complementary strands of equal or unequal length and wherein amplified nucleic acid molecule of step (A) may be present in such second sample:
  (e) subjecting the nucleic acid of a second sample to treatment which renders nucleic acid containing such exo-sample nucleotide substantially unamplifiable in an amplification dependent on such specific primers and which does not substantially affect amplification of nucleic acid that does not contain the exo-sample nucleotide;
whereby any primer extension products of such first sample, amplified in step (A) and present in such second sample, are not further substantially amplified in step (B).

Most particularly, the present invention is directed to a process for amplifying one or more nucleic acid molecules in a sample, comprising the steps of:
(A) with a first sample containing a nucleic acid molecule or a mixture of nucleic acid molecules, wherein each nucleic acid molecule has two separate complementary strands of equal or unequal length:
  (a) treating such strands with two oligonucleotide primers, for each different specific sequence being amplified, wherein at least one primer comprises deoxyuridine, under conditions such that for each different nucleic acid molecule being amplified an extension product of each primer is synthesized which is complementary to each nucleic acid strand, wherein such primers are selected so as to be sufficiently complementary to different strands of each specific nucleic acid molecule to hybridize therewith such that the extension product synthesized from one primer, when it is separated from its complement, can serve as a template for synthesis of the extension product of the other primer;
  (b) separating the primer extension products from the templates on which they were synthesized to produce single-stranded molecules;
  (c) treating such single-stranded molecules generated from step (b) with the primers of step (a) under conditions that a primer extension product is synthesized using each of the single strands produced in step (b) as a template;
  (d) repeating steps (a) through (c) at least once, thereby amplifying such specific nucleic acid molecule contained by the first sample;
(B) with a second sample containing a nucleic acid sequence or a mixture of nucleic acid sequences, wherein each nucleic acid sequence has two separate complementary strands of equal or unequal length and wherein amplified nucleic acid sequences of step (A) may be present in such second sample:
  (e) treating such strands with uracil DNA glycosylase;
  (f) terminating the action on the strands of the uracil DNA glycosylase by heating; and
  (g) repeating steps (a) through (c) at least once, thereby amplifying any of the specific nucleic acid sequence contained by second sample;
whereby any primer extension products of the first sample, amplified in steps (A) and present in such second sample, are not further substantially amplified in steps (B).

In addition, the present invention is directed to a method of detecting target nucleic acid in a sample comprising the steps of:
(a) providing nucleic acid of the sample as single-stranded nucleic acid;
(b) providing in the sample at least four DNA probes, wherein:
  (i) the first and second of said probes are primary probes, and the third and fourth of said probes are secondary nucleic acid probes;
  (ii) the first probe is a single strand capable of hybridizing to a first segment of a primary strand of the target nucleic acid;
  (iii) the second probe is a single strand capable of hybridizing to a second segment of said primary strand of the target nucleic acid sequence;
  (iv) the 5' end of the first segment of said primary strand of the target is positioned relative to the 3' end of the second segment of said primary strand of the target to enable joining of the 3' end of the first probe to the 5' end of the second probe, when said probes are hybridized to said primary strand of said target nucleic acid;
  (v) the third probe is capable of hybridizing to the first probe;
  (vi) the fourth probe is capable of hybridizing to the second probe;
  (vii) at least the 3' nucleotide of the first probe or the 5' nucleotide of the second probe is deoxyuridine; and
  (viii) at least the 3' nucleotide of the fourth probe or the 5' nucleotide of the third probe is deoxyuridine; and
(c) repeatedly performing the following cycle:
  (i) hybridizing said probes with nucleic acid in said sample;
  (ii) ligating hybridized probes to form reorganized fused probe sequences; and
  (iii) denaturing DNA in said sample; and
(d) detecting the reorganized fused probe sequences; whereby with successive cycles the quantity of reorganized fused primary and fused secondary probes is increased.

The aforementioned method may also comprise, according to the invention, an additional step of subjecting, before step (c), the sample to a treatment which renders amplified nucleic acid containing exo-sample nucleotide substantially unamplifiable in an amplification dependent on such specific probes and which does not substantially affect amplification of nucleic acid that does not contain the exo-sample nucleotide.

Definitions

Figure 1:
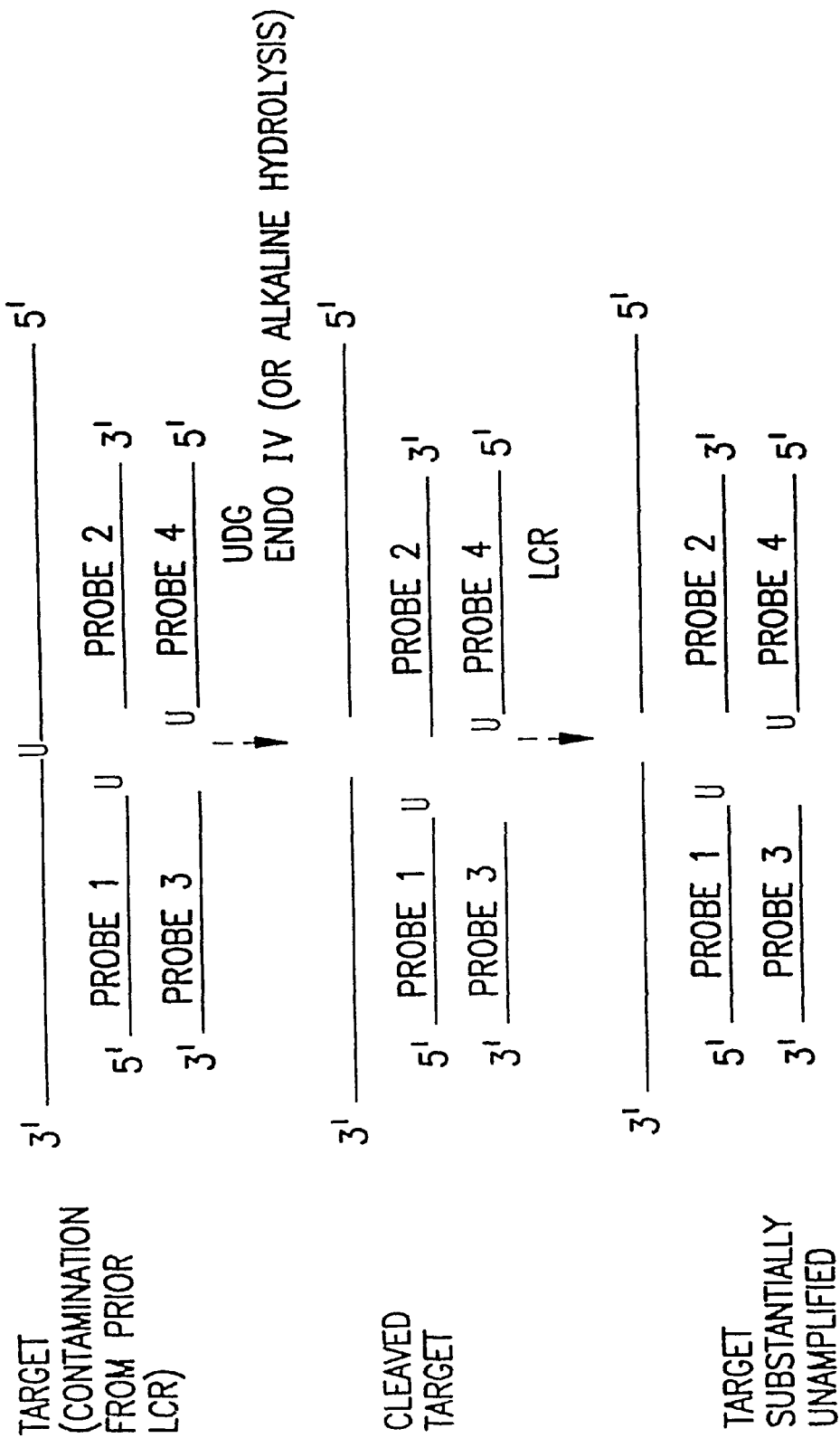
FIG. 1 shows a schematic of the application of exo-sample nucleotides in ligase chain reaction.

In the description that follows, a number of terms used in molecular biology and nucleic acid amplification technology are extensively utilized. In order to provide a clearer and consistent understanding of the specification and claims, including the scope to be given such terms, the following definitions are provided.

"Amplification," as used herein, refers to any in vitro process for increasing the number of copies of a nucleotide sequence or sequences. Nucleic acid amplification results in the incorporation of nucleotides into DNA or RNA. As used herein, one amplification reaction may consist of many rounds of DNA replication. For example, one PCR reaction may consist of 30–100 "cycles" of denaturation and replication.

"Nucleotide" as used herein, is a term of art that refers to a base-sugar-phosphate combination. Nucleotides are the monomeric units of nucleic acid polymers, i.e., of DNA and RNA. The term includes ribonucleoside triphosphates, such as rATP, rCTP, rGTP, or rUTP, and deoxyribonucleotide triphosphates, such as dATP, dCTP, dUTP, dGTP, or dTTP. A "nucleoside" is a base-sugar combination, i.e., a nucleotide lacking phosphate. It is recognized in the art that there is a certain inter-changeability in usage of the terms nucleoside and nucleotide. For example, the nucleotide deoxyuridine triphosphate, dUTP, is a deoxyribonucleoside triphosphate. After incorporation into DNA, it serves as a DNA monomer, formally being deoxyuridylate, i.e., dUMP or deoxyuridine monophosphate. One may say that one incorporates dUTP into DNA even though there is no dUTP moiety in the resultant DNA. Similarly, one may say that one incorporates deoxyuridine into DNA even though that is only a part of the substrate molecule.

"Exo-sample nucleotide," as used herein, refers to a nucleotide which is generally not found in the sample or sequence to be amplified. For most DNA samples, deoxyuridine is an example of an exo-sample nucleotide. Although the triphosphate form of deoxyuridine, dUTP, is present in living organisms as a metabolic intermediate, it is rarely incorporated into DNA. When dUTP is incorporated into DNA, the resulting deoxyuridine is promptly removed in vivo by normal processes, e.g., processes involving the enzyme uracil DNA glycosylase (UDG). Thus, deoxyuridine occurs rarely or never in natural DNA. It is recognized that some organisms may naturally incorporate deoxyuridine into DNA. For nucleic acid samples of those organisms, deoxyuridine would not be considered an exo-sample nucleotide. The presence of deoxyuridine, or any other exo-sample nucleotide, may be determined readily using methods well known to the art. Other exo-sample nucleotides may be envisioned. Numerous DNA glycosylases are known to the art. Any exo-sample nucleotide which may be incorporated into DNA during an amplification and a DNA glycosylase that acts on it may be used in this invention.

"Uracil DNA glycosylase" (UDG), a term of art, refers to an enzyme which cleaves the glycosidic bond between the base uracil and the sugar deoxyribose, only when the monomeric nucleotide dUTP is incorporated into a DNA molecule, resulting in incorporation of a deoxyuridine moiety (Duncan, B. in *The Enzymes* 14:565 (1981), ed.: Boyer P). The enzyme does not act upon free dUTP, free deoxyuridine, or RNA (Duncan, supra).

"Incorporating" as used herein, means becoming part of a nucleic acid polymer.

"Terminating" as used herein, means causing a treatment to stop. The term includes means for both permanent and conditional stoppages. For example, if the treatment is enzymatic, a permanent stoppage would be heat denaturation; a conditional stoppage would be, for example, use of a temperature outside the enzyme's active range. Both types of termination are intended to fall within the scope of this term.

"Oligonucleotide" as used herein refers collectively and interchangeably to two terms of art, "oligonucleotide" and "polynucleotide." Note that although oligonucleotide and polynucleotide are distinct terms of art, there is no exact dividing line between them and they are used interchangeably herein. The term "probe" may also be used interchangeably with the terms "oligonucleotide" and "polynucleotide."

"Oligonucleotide-dependent amplification" as used herein refers to amplification using an oligonucleotide or polynucleotide or probe to amplify a nucleic acid sequence. An oligonucleotide-dependent amplification is any amplification that requires the presence of one or more oligonucleotides or polynucleotides or probes that are two or more mononucleotide subunits in length and that end up as part of the newly-formed, amplified nucleic acid molecule.

"Primer" as used herein refers to a single-stranded oligonucleotide or a single-stranded polynucleotide that is extended by covalent addition of nucleotide monomers during amplification. Nucleic acid amplification often is based on nucleic acid synthesis by a nucleic acid polymerase. Many such polymerases require the presence of a primer that can be extended to initiate such nucleic acid synthesis.

"Substantially unamplifiable" as used herein refers to the inhibition of amplification of nucleic acids in any in vitro process. When the nucleic acid is said to be "substantially unamplifiable" the majority of the nucleic acid molecules ($\geq 50\%$) cannot be or are inhibited from being amplified, for example, by PCR or LCR. Although the term "substantially unamplifiable" indicates that the amplification of nucleic acid sequences is prevented or inhibited from being amplified, some amplification may still occur but such "background" amplification of a "substantially unamplifiable" nucleic acid can be distinguished from amplification of other nucleic acids which are "substantially amplifiable." Nucleic acids which are "substantially amplifiable" are, relatively speaking, amplified to a greater extent (at least two fold more) than "substantially unamplifiable" nucleic acids. One of ordinary skill in the art may easily utilize controls to distinguish between amplification of "substantially unamplifiable" nucleic acids and "substantially amplifiable" nucleic acids in accordance with the present invention.

DETAILED DESCRIPTION OF THE PREFERRED EMBODIMENTS

In the process according to the first embodiment, an amplification procedure is performed on a first sample in which one or more of the four normal ribonucleoside triphosphates (rNTPs) or deoxyribonucleoside triphosphates (dNTPs) is replaced with an exo-sample nucleotide. Before a second amplification, any contaminating amplified product that may be remaining is subjected to a physical, chemical, enzymatic, or biological treatment which renders nucleic acid containing the exo-sample nucleotide substantially unamplifiable. The treatment may be done as a separate step, or preferably, may be done in the presence of a second sample containing nucleic acid sequences to be amplified. The amplified nucleic acid sequences derived from the first sample which contaminate the second sample are not further substantially amplified during amplification of nucleic acid sequences of the second sample.

The deoxyribonucleoside triphosphate dUTP exemplifies an exo-sample nucleotide which may be conveniently incorporated into an enzymatic DNA amplification procedure, exemplified herein by PCR, thereby resulting in deoxyuridine-containing DNA. The DNA products of such a reaction will normally contain many uracil bases. Discrimination between natural DNA and the resultant, deoxyuridine-containing products of amplification procedures may be obtained with the enzyme uracil DNA glycosylase (UDG). Treatment of DNA containing uracil bases with uracil DNA glycosylase results in cleavage of the glycosidic bond between the deoxyribose of the DNA sugar-phosphate backbone and the uracil base. The loss of the uracil creates an apyrimidinic site in the DNA, which blocks DNA polymerase from using the DNA strand as a template for the synthesis of a complementary DNA strand (Schaaper, R., et al., *Proc. Natl. Acad. Sci. USA* 80:487 (1983)). The presence of substantial numbers of apyrimidinic sites in each DNA target molecule interferes with amplification procedures which use DNA polymerase to synthesize copies of target DNA. The DNA sugar-phosphate backbone that remains after UDG cleavage of the glycosidic bond can then be cleaved by endonuclease IV, alkaline hydrolysis, tripeptides containing aromatic residues between basic ones such as Lys-Trp-Lys and Lys-Tyr-Lys (Pierre et al., *J. Biol. Chem.* 256:10217–10226 (1981)) and the like.

As exemplified herein, the basic amplification protocol is the well known PCR method. PCR was modified in three ways: (1) dUTP was substituted for dTTP; (2) UDG was added to the initial PCR reaction mixture; and (3) an initial incubation period was added to allow UDG to destroy contaminating products of prior PCR reactions. The UDG itself was either permanently inactivated by high temperature in the first PCR cycle or was not active at the high temperatures used with Taq polymerase in the currently preferred PCR protocol. This inactivation prevents UDG from destroying newly-synthesized PCR products. Nucleic acid amplification protocols that do not eliminate UDG activity usually will require an extra UDG-inactivation step.

While termination of the physical, chemical, enzymatic, or biological treatment that renders nucleic acid containing the exo-sample nucleotide resistant to the amplification process is preferred (as exemplified herein, heat inactivation of UDG). the embodiment also includes variations lacking a termination step. For example, one might use amounts of enzyme and durations of treatment high enough to eliminate expected contamination of starting materials but insufficient to keep up with the rate of amplification. In other words, a treatment might be able to destroy contaminating nucleic acid but an amplification process might still be able to produce new nucleic acid faster than the treatment could destroy the newly synthesized nucleic acid.

Variations on the herein disclosed embodiment may also be envisioned. For example, the amplification may be done without an exo-sample nucleotide, i.e., using normal nucleotides. A normal nucleotide in the amplified DNA is then converted into an exo-sample nucleotide. The converted DNA can then be removed from any samples which it later contaminates. An example would be the conversion of neighboring pyrimidine residues, especially thymidine, into pyrimidine dimers (thymidine dimers), which make DNA unsuitable as a template. Thymidine dimers can also be removed by enzymes such as exonuclease VII and recBC.

The methods of the invention allow amplification products to be distinguished from the original nucleic acid substrate in a manner which does not interfere with detection analysis of such amplification products but which does make such amplification products uniquely susceptible to certain treatments which destroy their ability to serve as templates in subsequent amplification reactions. Because of this susceptibility, pretreating samples to be amplified according to the methods of this embodiment allows the elimination of any contaminating products of previous amplifications from the sample.

In the first embodiment, an exo-sample nucleotide is incorporated into amplification products during the amplification procedure itself so as to distinguish such amplified sequences from the original template.

In the second embodiment, the exo-sample nucleotide used to distinguish such amplification products herein is provided as part of an oligomer or polymer before amplification, while that of the first embodiment is provided as a nucleoside triphosphate which becomes incorporated into polymeric nucleic acid during amplification.

The methods of the second embodiment are applicable to any in vitro procedures which utilize enzymes to amplify specific nucleic acid sequences and especially to PCR and LCR.

In a preferred variation of the second embodiment, the nucleic acid products produced by an amplification which uses primers containing exo-sample nucleotides are chemically different from starting templates which were not produced by an amplification containing exo-sample nucleotides. This chemical difference permits one to render nucleic acid products, which were produced by an amplification which used primers containing exo-sample nucleotides, incapable of further exponential amplification.

Incorporation of an exo-sample nucleotide into a primer or probe allows the DNA or RNA produced during such amplification processes to be differentiated from the original nucleic acids present in the sample prior to amplification. If desired, the amplification reaction itself may, in addition, further provide exo-sample nucleotides for incorporation into the replicating nucleic acid.

Typically, oligonucleotides are used wherein one or more of the four ribonucleotides (ATP, UTP, CTP and GTP), or deoxyribonucleotides (dATP, dTTP, dCTP and dGTP), in the oligonucleotide are replaced with one or more exo-sample nucleotides. Embodiments utilizing oligonucleotides with high proportions of exo-sample nucleotides are preferred over those with fewer exo-sample nucleotide-containing oligonucleotides. Especially, oligonucleotides with a high fraction of exo-sample nucleotides located at the 3'OH end of the oligonucleotide are preferred. In another preferred embodiment, an exo-sample nucleotide is the 3' nucleotide.

In one variation of the second embodiment, treatment of exo-sample nucleotide primers to render amplified nucleic acid unamplifiable is performed before beginning an amplification reaction.

In another variation of the second embodiment, treatment to render amplified nucleic acid un-amplifiable is performed after terminating a first amplification reaction and after removing a sample of the amplified products for further analysis, but before subjecting the original, starting nucleic acid in the sample to a new, second amplification reaction. For example, after amplification and after removing amplified samples for analysis, amplified product that may be remaining is subjected to a treatment which renders amplified nucleic acid containing the exo-sample nucleotide substantially unamplifiable.

Such treatment to render the amplified nucleic acid containing the exo-sample nucleotide unamplifiable may be a physical, chemical, enzymatic, or biological treatment. Such treatment may be done as a separate step, or preferably, may be done in the presence of a second sample containing nucleic acid sequences to be amplified. Accordingly, amplified nucleic acid sequences produced by amplification of a first sample in the presence of exo-sample nucleotides which contaminate a second sample are not further substantially amplified during the second oligonucleotide-dependent amplification of nucleic acid sequences even if the same oligonucleotide(s) are used as primers or probes.

Discrimination between a nucleic acid which does not contain the exo-sample nucleotide deoxyuridine and a deoxyuridine-containing product of an amplification reaction may be obtained with the enzyme UDG. Treatment of DNA containing uracil bases with UDG results in cleavage of the glycosidic bond between the deoxyribose of the DNA sugar-phosphate backbone and the uracil base. The loss of the uracil creates an apyrimidinic site in the DNA, which blocks DNA polymerase from using the DNA strand as a template for the synthesis of a complementary DNA strand (Schaaper, R. et al. *Proc. Natl. Acad. Sci. USA* 80:487 (1983)). The presence of substantial numbers of apyrimidinic sites in each DNA target molecule interferes with amplification procedures which use DNA polymerase to synthesize copies of target DNA. The DNA sugar-phosphate backbone that remains after UDG cleavage of the glycosidic bond can then be cleaved by endonuclease IV, alkaline hydrolysis, tripeptides containing aromatic residues between basic ones such as Lys-Trp-Lys and Lys-Tyr-Lys (Pierre et al., *J. Biol. Chem.* 256:10217–10226 (1981) and Doetsch et al. *Mutation Research* 236:173–201 (1990)) and the like.

By providing primers containing exo-sample nucleotides, such exo-sample nucleotides are localized at the 5' ends of each strand of DNA template which is amplified. When deoxyuridine-containing primers have been used and the sample treated with UDG, substantial numbers of apyrimidinic sites in the 5'-end of each DNA target template molecule are found. Such apyrimidinic sites interfere with extension at the 3'-end of newly made strands. These 3'-end sequences are the targets to which original exo-sample-containing primers bind. Thus these primers do have target sequences with which they can bind a nucleic acid derived from molecules primed by exo-sample nucleotide-containing primers.

Oligonucleotides that contain deoxyuridine at or near their termini are not substantially susceptible to UDG cleavage of the glycosidic bond between the deoxyribose of the DNA sugar-phosphate backbone and the uracil base. Thus, particularly in LCR reactions, such oligonucleotides containing deoxyuridine at or near their termini are amplifiable even after treatment with UDG.

After amplification, preferably by LCR, the joined or ligated oligonucleotides (probes) containing deoxyuridine are substantially cleaved by UDG, thereby forming an apyrimidinic deoxyribose in a sugar-phosphate backbone of the ligated or joined oligonucleotides. The resulting sugar-phosphate backbone can be cleaved by treatment with endonuclease IV, alkaline hydrolysis, tripeptides containing aromatic residues between basic ones (Pierre et al., *J. Biol. Chem.* 256:10271–10220 (1991)) and the like. Thus, UDG treatment, and optionally the cleavage of the sugar-phosphate backbone, substantially prevents amplification of the ligation product, thereby allowing one to distinguish and eliminate such amplification products as possible contaminants from subsequent amplification reactions.

Other exo-sample nucleotides than deoxyuridine, exemplified herein, may be envisioned. Numerous DNA glycosylases are known to the art. An exo-sample nucleotide which may be chemically or enzymatically incorporated into an oligonucleotide and a DNA glycosylase that acts on it may be used in this invention. Other exo-sample nucleotides will be evident to those in the art. For example, RNA primers used for DNA amplifications can be readily destroyed by base or an appropriate ribonuclease (RNase). RNase H degrades RNA of RNA:DNA hybrids and numerous single-stranded RNases are known which are useful to digest single-stranded RNA after a denaturation step. (Note that unless the DNA strand opposite the RNA primer is removed by a single-stranded deoxyribonuclease (DNase) after RNase H digestion of the contaminating DNA but before denaturation thereof, the contaminating DNA will be amplified in a linear fashion. However, since most oligonucleotide-dependent DNA amplifications schemes amplify DNA exponentially, this will not be a problem unless the contamination levels are extraordinarily high. Those of ordinary skill in the art who are developing RNA-primed variations of the invention will be able to determine, without undue experimentation, the lowest acceptable level of contamination in their assays.)

In another embodiment deoxyoligonucleotides containing bromodeoxyuridine (BdUR) is used as the exo-sample nucleotide. DNA containing BdUR may be degraded on exposure to light under appropriate conditions.

As exemplified herein, in a preferred variation of the second embodiment, the basic amplification protocol PCR is modified in three ways; (1) amplification is first performed using oligonucleotide primers containing deoxyuracil substituted for deoxythymidine and samples of the amplified products are removed for analysis; (2) UDG is then added to subsequent PCR reaction mixtures; and (3) an incubation period is added to allow UDG to act on uracil-containing sequences in contaminating products from prior PCR reactions.

As exemplified herein, in another preferred variation of the second embodiment, the basic amplification protocol LCR is modified in three ways:
(1) amplification is first performed using oligonucleotide probes containing deoxyuracil substituted for deoxythymidine at or near at least one terminus of the oligonucleotides and samples of the amplified products are removed for analysis;
(2) UDG is then added to subsequent LCR reaction mixtures; and (3) an incubation period is added to allow UDG to act on uracil-containing sequences in contaminating products from prior LCR reactions. The UDG treatment alone has been found to substantially prevent amplification of the uracil-containing ligation product without substantially affecting amplification of the oligonucleotide probes containing deoxyuracil near the end of the probes. As an alternative to UDG treatment alone, UDG and a treatment that cleaves the sugar-phosphate backbone (remaining after UDG treatment) may be used. Such treatments that cleave the sugar-phosphate backbone may include, but are not limited to, endonuclease IV, alkaline hydrolysis, tripeptides such as Lys-Trp-Lys and Lys-Tyr-Lys (Pierre et al., *J. Biol. Chem.* 256:10217–10220 (1981)), AP endonucleases such as endonuclease V, endonuclease III, endonuclease VI, endonuclease VII, human endonuclease II, and the like (Linn, S. *Nucleases Involved in DNA Repair* in Nucleases, Cold Spring Harbor Laboratory, ed. Linn, S. and Roberts, R. (1985)).

Before continuing with the amplification procedure, the UDG and the enzyme treatment to cleave the sugar-phosphate backbone (if present) should be inactivated. UDG and the enzyme treatment to cleave the sugar-phosphate backbone may be either permanently inactivated by high temperature in the first PCR or LCR cycle, or by the high temperatures used with Taq DNA polymerase or Taq DNA ligase in the currently preferred PCR or LCR protocols, respectively. This inactivation prevents UDG from destroying newly-synthesized PCR or LCR products. Nucleic acid amplification protocols that do not inherently eliminate UDG activity usually will require an extra UDG-inactivation step.

Embodiments having a greater proportion of oligonucleotides containing exo-sample nucleotides are preferred. However, even in standard PCR embodiments that depend on two oligonucleotide primers, the present invention is capable of rendering PCR contaminants unamplifiable as long as at least one primer contains an exo-sample nucleotide.

Not all single exo-sample nucleotide-containing oligonucleotides may reduce amplification of PCR or LCR products to sufficiently low levels for a given situation; those of ordinary skill in the art can empirically find which primers or probes are acceptable during routine optimization and testing of a PCR or LCR assay, without undue experimentation.

Routine assay optimization, aimed at testing oligonucleotide suitability, can be done by (1) making an exo-sample nucleotide-containing oligonucleotide, (2) performing a first nucleic acid amplification of a target sequence using that oligonucleotide, (3) seeding various amounts of the resulting first product in a new, second amplification that does not contain target sequences, (4) treating the second amplification to render exo-sample nucleotide-containing nucleic acid unamplifiable, (5) performing the second amplification, and (6) assaying the resultant second product for presence of contaminating sequence from the first hybridization. All of these steps are routinely done as experimental controls and as part of the normal validation of a method. The only additional work required of one practicing this embodiment involves routine synthesis of any additional oligonucleotides that may be required. Generally, if a oligonucleotide is observed to be not suitable, a substitute can be easily found and similarly tested.

As will be understood by those of ordinary skill in the art, the methods of the invention prevent exponential amplification but may not prevent linear amplification. Linear amplification does not usually represent a substantial problem in amplification procedures. For example, a single amplification product molecule which contaminates a sample run through 20 cycles of PCR, amplifying by a factor of two on each cycle, will result in only about 20 molecules if amplified linearly but could result in up to about a million molecules if amplified exponentially at maximal theoretical efficiency. Thus, linear amplification is generally inconsequential.

The second embodiment can be adapted to be used with amplifications that do not use a nucleic acid polymerase. For instance, as exemplified herein, contamination of samples with previously made products can be controlled by amplification schemes that polymerize oligonucleotides with ligase (e.g., Wu and Wallace, supra, and Barany, *Proc. Natl. Acad. Sci. USA* 88:189–193 (199)).

The present invention is also ideally suited for preparation of a kit. Such a kit may comprise a carrier means being compartmentalized to receive in close confinement one or more container means such as vials, test tubes, bottles, and the like. Each of said container means may comprise an oligonucleotide containing exo-sample nucleotide such as an oligonucleotide containing deoxyuridine, an exo-sample nucleotide such as deoxyuridine, a nucleic acid ligase, a nucleic acid polymerase, a uracil DNA glycosylase and the like. As will be evident, the components included in a kit such as a nucleic acid ligase, a uracil DNA glycosylase etc. may be mixed in various combinations and such combinations may be included in a single or multiple container means.

Having now generally described this invention, the same will be better understood by reference to certain examples which are included herein for purposes of illustration only and is not intended to be limiting unless otherwise specified.

EXAMPLES

Example 1

A polymerase chain reaction (PCR) was performed to amplify a region of the human papilloma virus type 16 (HPV 16) DNA (Durst, M. et. al., *Proc. Natl. Acad. Sci. USA* 80:3812 (1983)). The sequences of the primers used were 5'GGTCGATGTATGTCTTGTTG3' (SEQ ID NO:1) and 5'GTCTACGTGTGTGCTTTGTAC3' (SEQ ID NO:2).

HPV 16 DNA was excised from a full length plasmid clone, pT7HPV16 (for the purposes of this invention, equivalent to the pUC8 plasmids described by Seedoff, K., et al., *Virol.* 145:181 (1985)) with the restriction enzyme BamHl. The linear DNA (10 picograms) was added to PCR reactions containing 50 microliters of 25 mM Tris HCl pH 8.3, 5 mM $MgCl_2$, 50 mM NaCl, 0.01% gelatin, 0.05% W1 polyoxyethylene ether detergent (Sigma), 0.2 mM each dATP, dGTP, dCTP, 0.2 mM either dUTP or dTTP, 1 micromolar of each primer, and 2.5 units of thermostable DNA polymerase from *Thermus aqualicus* (Cetus/Perkin-Elmer). The reactions were amplified in a thermal cycler (Cetus/Perkin-Elmer) using the following temperature profile: 5 minutes at 94° C., then 30 cycles of 1 minute at 94° C. (denaturation), two minutes at 55° C. (annealing), and 3 minutes at 72° C. (primer extension). After completion of the temperature cycles, a final extension of 10 minutes at 72° C. was done. Amplification of the 284 base pair HPV 16 DNA fragment was confirmed by agarose/ethidium bromide gel electrophoresis (Maniatis, T., et al., *Molecular Cloning*, Cold Spring Harbor Laboratory (1982)) of the PCR reaction products (5 microliters of each reaction per lane). All reactions showed substantial amplification. Negative control reactions to which no HPV 16 DNA was added did not produce any visible DNA products.

The concentration o f the PCR amplification products was estimated from the agarose gel. New PCR reactions were contaminated with ten femtogram quantities of the amplification products that contained either deoxythymidine, resulting from incorporation of dTTP, or deoxyuridine, from dUTP-containing reactions. Positive control reactions contained 10 picograms of linear HPV 16 DNA. Negative control reactions did not receive any target DNA. The new PCR reactions contained dUTP instead of dTTP, and either 5 nanograms of UDG (Van de Sande, H., University of Calgary; also available from Life Technologies Inc., P.O. Box 9418, Gaithersburg, Md., 20898) or no UDG. All reactions were incubated for 15 minutes at 37° C. to allow the UDG to act on deoxyuridine-containing DNA, and then were taken through the same thermal cycling protocol as above. Aliquots of each reaction were analyzed by agarose/ethidium bromide gel electrophoresis.

The agarose gel analysis showed that without UDG treatment the deoxyuridine-containing PCR products could be re-amplified to give a DNA product virtually indistinguishable in size, as evidenced by gel electrophoresis, from the products obtained by amplifying the normal HPV 16 DNA. Reactions in which the deoxyuridine-containing DNA was incubated with UDG prior to PCR did not give any visible products on the agarose gel. PCR amplification products that contained deoxythymidine were successfully amplified whether or not they had been incubated with UDG. This experiment showed that UDG substantially abolished amplification of PCR products containing deoxyuridine, but had no substantial effect on the amplification of DNA containing deoxythymidine.

Although the foregoing refers to particular preferred variations of the first embodiment, it will be understood that this embodiment is not so limited. It will occur to those of ordinary skill in the art that various modifications may be made to the disclosed embodiments and that such modifications are intended to be within the scope of this embodiment.

Example 2

General Experimental Conditions of the Second Embodiment

Polymerase chain reactions (PCRs) were performed to amplify a region of the human papilloma virus type 16 (HPV 16) DNA (Durst, M. et al. *Proc. Natl. Acad. Sci. USA* 80:3812(1983)). The sequences of the oligonucleotide primers used were either 5'GGUCGAUGUAUGUCUUGUUG3' (SEQ ID NO:3) and 5'GUCUACGUGUGUGCUUU-GUAC3' (SEQ ID NO:4) (dU primers $dU_1$ and $dU_2$, respectively) or 5'GGTCGATGTATGTCTTGTTG3' (SEQ ID NO:1) and 5'GTCTACGTGTGTGCTTTGTAC3' (SEQ ID NO:2) (control dT primers $dT_1$ and $dT_2$, respectively). Note that the sequences of $dT_1$ and $dU_1$ were identical except for the replacement of U for T; $dT_2$ and $dU_2$ were similarly identical.

HPV 16 DNA was excised from a full length plasmid clone, pT7HPV16 (for the purposes of this invention, equivalent to the pUC8-based plasmids described by Seedoff, K. et al. *Virol.* 145:181 (1985)) with the restriction enzyme BamHl. The linear DNA (10 picograms) was added to PCR reactions containing 50 microliters of 25 mM Tris HCl pH 8.3, 5 mM $MgCl_2$, 50 mM NaCl, 0.01% gelatin, 0.2 mM each dATP, dGTP, dCTP, 0.2 mM either dUTP or dTTP. 1 micromolar of each primer, and 2.5 units of thermostable DNA polymerase from *Thermus aquaticus*(Cetus/Perkin-Elmer). Primers and triphosphates were paired as follows: dU primers with dTTP (pUxT reactions ("primed with U, extended with T")) and control dT primers with dUTP (pTxU reactions). The reactions were amplified in a thermal cycler (Cetus/Perkin-Elmer) using the following temperature profile: 5 minutes at 94° C., then 30 cycles of I minute at 94° C. (denaturation), two minutes at 55° C. (annealing), and 3 minutes at 72° C. (primer extension). After completion of the temperature cycles, a final extension of 10 minutes at 72° C. was done. Amplification of the 284 base pair HPV 16 DNA fragment was confirmed by agarose/ethidium bromide gel electrophoresis (Maniatis, T., et al., *Molecular Cloning,* Cold Spring Harbor Laboratory (1982)) of the PCR reaction products (5 microliters of each reaction per lane). All reactions showed substantial amplification. Negative control reactions to which no HPV 16 DNA was added did not produce any DNA products. The concentration of the PCR amplification products was estimated from the agarose gel.

Example 3

Amplification Using Two Deoxyuridine-Containing Primers

New pUxT PCR reactions were prepared that contained dTTP but lacked dU primers. These were contaminated with ten femtograms of pUxT amplification products from the previous reactions, and incubated for 15 minutes at 37° C. in the presence or absence of UDG (H. Van de Sande, University of Calgary; also available from Life Technologies Inc., P.O. Box 9418, Gaithersburg, Md. 20898). These reactions were then incubated at 94° C. to inactivate the UDG, cooled to 15° C., and dU primers were added.

New pTxU PCR reactions were prepared with dT primers and dUTP and were contaminated with ten femtograms of pTxU amplification products. These reactions were incubated at 37° C. for 15 minutes in the presence or absence of UDG to act as controls for UDG activity and PCR amplification, respectively.

The new PCR reactions were then subjected to the same PCR temperature cycling described above. Agarose/ethidium bromide gel electrophoresis showed that in the absence of UDG treatment both pUxT and pTxU reaction products could be reamplified by PCR to give results identical in appearance to those obtained upon amplification of HPV 16 DNA. In contrast, UDG treatment abolished reamplification of both pTxU reaction products (the positive control) and pUxT reaction products, which contained dU primers. In another experiment it was shown that, in the absence of deoxyuridine in either the primers or extension products. UDG did not affect the PCR amplification of natural HPV 16 DNA.

Without UDG treatment, the deoxyuridine-containing PCR products could be re-amplified to give a DNA product virtually indistinguishable in size, as evidenced by agarose gel electrophoresis, from the products which did not contain deoxyuridine and which were obtained by amplifying the normal HPV 16 DNA. The reaction in which the DNA was made with deoxyuridine-containing primers and which was incubated with UDG prior to PCR did not substantially give any visible products on the agarose gel. In another experiment it was shown that UDG did not affect the amplification of natural DNA.

Example 4

Amplification Using a Single Deoxyuridine-Containing Primer

A further experiment demonstrated that only one of two PCR primers need contain an exo-sample nucleotide. PCR amplifications were done essentially as described above using the following pairs of primers: (1) $dT_1$ with $dT_2$, (2) $dT_1$ with $dU_2$, (3) $dU_1$ with $dT_2$, and (4) $dU_1$ with $dU_2$. All combinations of PCR products were treated both with and without UDG before the second round of PCR. Amplification (1) tested for success of PCR amplification while amplification (4) tested for activity of UDG and the ability to eliminate contamination. Amplification (3) was observed to not be substantially reamplified after UDG treatment in a second round of PCR, thereby demonstrating that only one of a pair of PCR primers need contain an exo-sample nucleotide in order to reduce or eliminate the effects of sample contamination. Amplification (2) was observed to be reamplified, though at a substantially lower level than amplification (1).

Summary

In summary, PCR amplification products that contained deoxyuridine in a primer or primers were successfully amplified if no UDG was present; amplification could be prevented by prior incubation with UDG. In other words, UDG could substantially abolish amplification of PCR products made with deoxyuridine-containing primers but had no substantial effect on the amplification of DNA made with deoxythymidine-containing primers.

Example 5

A modification of the Ligase Chain Reaction (LCR) described by Barany (F. Barany, *Proc. Natl. Acad. Sci.* 88, 189–193, 1991) was performed to amplify a region of the human beta globin gene. A schematic of this experiment demonstrating the application of exo-sample nucleotides in LCR is shown in FIG. 1.

The sequences of the probe oligonucleotides were:

1088 (probe 4): 5' acc atg gtg cac ctg act ccu 3'  (SEQ ID NO:5)

1089 (probe 3): 5' gag gag aag tct gcc gtt act 3'  (SEQ ID NO:6)

1090 (probe 2): 5' cag gag tca ggt gca cca tg 3'  (SEQ ID NO:7)

1091 (probe 1): 5' cag taa cgg cag act tct ccu 3'  (SEQ ID NO:8)

The sequence of the target oligonucleotide was:

1092 (target): 5' gac acc atg gtg cac ctg act ccu gag gag aag tct gcc gtt act gcc ctg 3'  (SEQ ID NO:9)

Oligonucleotides were chemically synthesized by standard techniques. They were trace labeled with $^{32}$P (approximately 30 dpm/pmol each oligonucleotide) and gel purified, and their quantities were estimated by hybridization and electrophoresis on 5% agarose/ethidium bromide gels. Thermostable DNA ligase from *Thermus aquaticus* was purchased from Molecular Biology Resources (MBR), Milwaukee, Wis. UDG was from Life Technologies, Inc., Gaithersburg, Md. The buffer used was that suggested by MBR, and contained 20 mM Tris HCl pH 7.5, 25 mM KCl, 10 mM MgCl$_2$, 10 mM dithiothrcitol, 0.6 mM NAD, 0.1% Triton X100. Probe oligonucleotide #1089 was labeled at its 5' terminus with $^{32}$P using T4 polynucleotide kinase to a specific activity of about 250,000 dpm per picomole, then chased with unlabeled rATP and the kinase was heat inactivated. The final concentration of the labeled #1089 oligonucleotide was about 1 picomole per microliter. Oligonucleotide #1090 was phosphorylated at its 5' end with rATP and T4 polynucleotide kinase.

Reactions for UDG treatment contained 20 pmol each of all four trace labeled probe oligos with or without 2 pmol target. These samples were incubated in 10 μl 50 mM Tris HCl pH 8.0, 1 mM EDTA under oil for 15 min at 37° in the presence or absence of 0.5 μl=0.5 units UDG, as follows:

A: Probes only, no UDG
B: Probes only,+UDG
C: Probes+target, no UDG (should support LCR)
D: Probes+target+UDG (target degraded, no LCR)
E: Probes only,+UDG Any abasic sites (apyrimidinic sites) produced by UDG were broken (i.e., cleavage of the sugar phosphate backbone) by alkaline hydrolysis as follows: to all five tubes was added 5 μl 0.2 M NaOH giving a pH of about 13. The tubes were incubated at 95° for 10 minutes, cooled, and 5 μl of 2.5% acetic acid were added to bring the pH back to about 5. Any target (oligo #1092) present in the reactions was cleaved by the combination of base removal by UDG and breakage of the sugar-phosphate backbone by elevated temperature and pH.

At this time (after UDG inactivation by alkaline pH and heat) 1 μl (2 pmol) target (#1092) was added to reaction E. Thus the target in reaction "E" was never exposed to active UDG, but only to inactivated UDG.

The concentrations of the salt produced by the alkaline hydrolysis reactions were reduced to avoid interference with subsequent ligase reactions and gel electrophoresis. Five μl of each reaction were diluted 1:40 in 1×MBR buffer (20 mM Tris HCl pH 7.5, 25 mM KCl, 10 mM MgCl$_2$, 10 mM dithiothreitol, 0.6 mM NAD, 0.1% Triton X100). To 20 μl each diluted oligo mixture was added 0.5 μl=500 fmol $^{32}$P-labeled #1089 to follow the progress of the LCR reactions. Four μl of these mixtures containing 100 fmol probes 5'OH-1088, 5'P-1090, and 5'-OH-1091, 200 fmol 5'-$^{32}$P 1089, with or without 10 fmol 5'OH-target #1092, were aliquotted to pairs of tubes and 16 μl of 1×MBR buffer with ("+") or without ("-") 10 units of MBR Taq ligase were added. A drop of oil was added to the 20 μl reactions and they were cycled 85°30s, 50° 20 min, 20 times in a Cetus/Perkin Elmer Thermal Cycler. 2.5 μl each reaction were applied to a 12% denaturing sequencing gel using standard techniques (Maniatis, supra).

Following electrophoresis and exposure of the gel to X-ray film, the following results in the presence of ligase were observed:

The "A" reaction (probes only, no UDG treatment) showed a minimal amount (about 5% of the starting probes) of target-independent amplification (i.e., ligation product of about 40 nucleotides was produced).

The "B" reaction (probes treated with UDG) showed minimal target-independent amplification indistinguishable from reaction "A." This indicated that UDG had no effect on the integrity of the probes.

The "C" reaction (containing probes and target without UDG treatment) showed the majority (about 70%) of the probes were converted to product by target-dependent ligation.

Reaction "D" (containing probes and target treated with UDG) showed substantial decrease in the amount of ligation product present. This was the expected result if the uracil in the target had been removed by UDG and the sugar-phosphate backbone had been broken by elevated pH and temperature treatment (FIG. 1).

Reaction "E" (probes treated with UDG, and target added after UDG inactivation by pH and heat) showed the majority of the probes (about 70%) had been ligated to form product. This result demonstrated that the probes had not been affected by the UDG treatment, allowing them to participate in the ligation reactions.

The amounts of product produced in reactions C, D, and E show that UDG is active on a uracil positioned in the sequence of target oligonucleotide (i.e., not at the terminus), but is inactive on uracils at the 3' termini of oligonucleotides. It has also been demonstrated that UDG had relatively little activity on uracils located at the 5' terminus of an oligonucleotide.

To confirm the presence of uracil at the 3' terminus of probe #1088, products of reactions C and E were pooled, precipitated with ethanol, and dissolved in 20 µl of water. One µl of 1 M Tris HCl pH 8.0 and one µl of 20 mM EDTA were added to the pooled oligonucleotides and two 5 µl aliquots were placed in tubes. To one tube, 0.5 µl (0.5 units) BRL UDG were added. To the other was added 0.5 µl water. Both tubes were incubated at 37° C. for 15 minutes, and to each was added 1 µl 1 N NaOH. The tubes were incubated at 95° for 15 minutes and 1 µl 12.5% acetic acid was added to neutralize the mixtures. About one third of each reaction was applied to a 12% sequencing gel. The presence of the 3+ dU of oligonucleotide #1088 was confirmed by the UDG-specific cleavage of the LCR products. The size of the cleavage product was precisely that expected from the structures of the participating oligonucleotides. In other words, the ligation product of oligonucleotides 1088 and 1089 was cleaved by the combination of UDG and elevated pH and temperature, indicating that a uracil was present at the ligation junction of the participating oligonucleotides.

Summary

Uracil bases located at certain positions within oligodeoxynucleotides, especially at or near the 5' and 3+ ends, were not removed by the enzyme uracil DNA glycosylase. This can be the basis of a method to control carryover contamination of Ligation Chain Reaction amplifications, if the uracil bases at these certain locations become sensitive to UDG when the oligodeoxynucleotide(s) become incorporated into LCR products.

In the example described here, deoxyuracil bases at the 3' ends of oligodeoxynucleotides are not recognized by UDG. Once the oligonucleotides containing the 3' deoxyuracil was joined or ligated by LCR, the ligation products became sensitive to cleavage with UDG and alkaline hydrolysis. Thus, this treatment rendered the amplification products unamplifiable in subsequent LCR reactions.

Example 6

A modification of LCR as described in Example 5 was performed to determine the ability of UDG alone (without alkaline hydrolysis of the sugar-phosphate backbone) to prevent amplification of uracil-containing amplification products.

20 µl reactions contained as indicated 100 fmol probe oligos (1088 and 1091 with 5' OH and 3' dU; 1089 and 1090 with 5' phosphate; 1089 labeled with $^{32}$P); 5 fmol target #1092 (internal dU) or #1058 (no dU); 5 units Taq ligase; and 0.25 ul BRL UDG.

Reactions were assembled and incubated under mineral oil in a Cetus/Perkin-Elmer Thermal Cycler: 37° C. 90 min, 85° C. 5 min, then 20 cycles of 85° C. 30 sec, 55° C. 2 min, followed by incubation at 0° C.

1.25 µl aliquots of each reaction were applied to a 12.5% polyacrylamide/8 M urea gel and electrophoresed at 70 watts power for about 90 minutes. An autoradiograph was made of the wet gel at −70° C. using an intensifying screen.

In the absence of target, about 5% of the probe oligo was ligated to larger product. This represents target-independent background. In the presence of 5 fmol of target, about 70 fmol of probe oligo (70% of the total present in the reaction) ligated to form product. When 0.25 µl of UDG were present in the reaction containing dT target, no effect was observed on the amount of ligation product obtained (about 70 fmol). In contrast, only about 10 fmol of ligation product was obtained when UDG was incubated with dU target (mock contaminant). These observations show that the 3' dU of oligos 1088 and 1091 were not affected by the UDG, and that greater than 90% of the dU mock contaminant was converted by UDG incubation to a form that could not be a substrate for ligation of probe oligonucleotides.

Summary

UDG treatment of uracil-containing "ligation products" (#1092) were substantially prevented from being amplified during Ligase Chain Reaction. However, uracil-containing "ligation products" not treated with UDG were amplified. Thus, UDG incubation alone. without further treatment, is sufficient to substantially prevent amplification of uracil-containing ligation contaminants which may be present in subsequent LCR reaction samples.

All documents cited herein are incorporated by reference. Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

What is claimed is:

1. An amplification mixture comprising one or more exo-sample nucleotides and a primer.
2. The amplification mixture of claim 1, wherein said one or more exo-sample nucleotides is deoxyuridine.
3. The amplification mixture of claim 1, wherein said one or more exo-sample nucleotides is bromodeoxyuridine.
4. The amplification mixture of claim 1 further comprising a DNA polymerase.
5. The amplification mixture of claim 4, wherein said DNA polymerase is a Taq DNA polymerase.
6. The amplification mixture of claim 1 further comprising one or more nucleotides.
7. The amplification mixture of claim 1 further comprising a DNA glycosylase.
8. The amplification mixture of claim 7, wherein said DNA glycosylase is a uracil DNA glycosylase.
9. The amplification mixture of claim 1 further comprising a DNA polymerase, one or more nucleotides, and a DNA glycosylase.
10. An amplification kit comprising one or more exo-sample nucleotides and a primer.
11. The amplification kit of claim 10, wherein said one or more exo-sample nucleotides is deoxyuridine.
12. The amplification kit of claim 10, wherein said one or more exo-sample nucleotides is bromodeoxyuridine.
13. The amplification kit of claim 10 further comprising a DNA polymerase.
14. The amplification kit of claim 13, wherein said DNA polymerase is a Taq DNA polymerase.
15. The amplification kit of claim 10 further comprising one or more nucleotides.
16. The amplification kit of claim 10 further comprising a DNA glycosylase.
17. The amplification kit of claim 16, wherein said DNA glycosylase is a uracil DNA glycosylase.
18. The amplification kit of claim 10 further comprising a DNA polymerase, one or more nucleotides, and a DNA glycosylase.
19. A nucleic acid synthesis mixture comprising one or more exo-sample nucleotides and a primer.
20. The nucleic acid synthesis mixture of claim 19, wherein said one or more exo-sample nucleotides is deoxyuridine.
21. The nucleic acid synthesis mixture of claim 19, wherein said one or more exo-sample nucleotides is bromodeoxyuridine.
22. The nucleic acid synthesis mixture of claim 19 further comprising a DNA polymerase.
23. The nucleic acid synthesis mixture of claim 22, wherein said DNA polymerase is a Taq DNA polymerase.
24. The nucleic acid synthesis mixture of claim 19 further comprising one or more nucleotides.
25. The nucleic acid synthesis mixture of claim 19 further comprising a DNA glycosylase.
26. The nucleic acid synthesis mixture of claim 25, wherein said DNA glycosylase is a uracil DNA glycosylase.
27. The nucleic acid synthesis mixture of claim 19 further comprising a DNA polymerase, one or more nucleotides, and a DNA glycosylase.
28. A nucleic acid synthesis kit comprising one or more exo-sample nucleotides and a primer.
29. The nucleic acid synthesis kit of claim 28, wherein said one or more exo-sample nucleotides is deoxyuridine.
30. The nucleic acid synthesis kit of claim 28, wherein said one or more exo-sample nucleotides is bromodeoxyuridine.
31. The nucleic acid synthesis kit of claim 28 further comprising a DNA polymerase.
32. The nucleic acid synthesis kit of claim 31, wherein said DNA polymerase is a Taq DNA polymerase.
33. The nucleic acid synthesis kit of claim 28 further comprising one or more nucleotides.
34. The nucleic acid synthesis kit of claim 28 further comprising a DNA glycosylase.
35. The nucleic acid synthesis kit of claim 34, wherein said DNA glycosylase is a uracil DNA glycosylase.
36. The nucleic acid synthesis kit of claim 28 further comprising a DNA polymerase, one or more nucleotides, and a DNA glycosylase.
37. An amplification mixture comprising one or more exo-sample nucleotides and a DNA glycosylase.
38. The amplification mixture of claim 37, wherein said one or more exo-sample nucleotides is deoxyuridine.
39. The amplification mixture of claim 37, wherein said one or more exo-sample nucleotides is bromodeoxyuridine.
40. The amplification mixture of claim 37, wherein said DNA glycosylase is a uracil DNA glycosylase.
41. The amplification mixture of claim 37 further comprising a DNA polymerase.
42. The amplification mixture of claim 41, wherein said DNA polymerase is a Taq DNA polymerase.
43. The amplification mixture of claim 37 further comprising one or more nucleotides.
44. The amplification kit of claim 37 further comprising a primer.
45. The amplification mixture of claim 37 further comprising a DNA polymerase, one or more nucleotides, and a primer.
46. An amplification kit comprising one or more exo-sample nucleotides and a DNA glycosylase.
47. The amplification kit of claim 46, wherein said one or more exo-sample nucleotides is deoxyuridine.
48. The amplification kit of claim 46, wherein said one or more exo-sample nucleotides is bromodeoxyuridine.
49. The amplification kit of claim 46, wherein said DNA glycosylase is a uracil DNA glycosylase.
50. The amplification kit of claim 46 further comprising a DNA polymerase.
51. The amplification kit of claim 50, wherein said DNA polymerase is a Taq DNA polymerase.
52. The amplification kit of claim 46 further comprising one or more nucleotides.
53. The amplification kit of claim 46 further comprising a primer.
54. The amplification kit of claim 46 further comprising a DNA polymerase, one or more nucleotides, and a primer.
55. A nucleic acid synthesis mixture comprising one or more exo-sample nucleotides and a DNA glycosylase.
56. The nucleic acid synthesis mixture of claim 55, wherein said one or more exo-sample nucleotides is deoxyuridine.
57. The nucleic acid synthesis mixture of claim 55, wherein said one or more exo-sample nucleotides is bromodeoxyuridine.
58. The nucleic acid synthesis mixture of claim 55, wherein said DNA glycosylase is a uracil DNA glycosylase.
59. The nucleic acid synthesis mixture of claim 55 further comprising a DNA polymerase.
60. The nucleic acid synthesis mixture of claim 59, wherein said DNA polymerase is a Taq DNA polymerase.
61. The nucleic acid synthesis mixture of claim 55 further comprising one or more nucleotides.
62. The nucleic acid synthesis mixture of claim 55 further comprising a primer.

63. The nucleic acid synthesis mixture of claim 55 further comprising a DNA polymerase, one or more nucleotides, and a primer.

64. A nucleic acid synthesis kit comprising one or more exo-sample nucleotides and a DNA glycosylase.

65. The nucleic acid synthesis kit of claim 64, wherein said one or more exo-sample nucleotides is deoxyuridine.

66. The nucleic acid synthesis kit of claim 64, wherein said one or more exo-sample nucleotides is bromodeoxyuridine.

67. The nucleic acid synthesis kit of claim 64, wherein said DNA glycosylase is a uracil DNA glycosylase.

68. The nucleic acid synthesis kit of claim 64 further comprising a DNA polymerase.

69. The nucleic acid synthesis kit of claim 68, wherein said DNA polymerase is a Taq DNA polymerase.

70. The nucleic acid synthesis kit of claim 64 further comprising one or more nucleotides.

71. The nucleic acid synthesis kit of claim 64 further comprising a primer.

72. The nucleic acid kit of claim 64 further comprising a DNA polymerase, one or more nucleotides, and a primer.

* * * * *

SEQUENCE LISTING

<160> NUMBER OF SEQ ID NOS:    9

<210> SEQ ID NO 1
<211> LENGTH: 20
<212> TYPE: DNA
<213> ORGANISM: Primer

<400> SEQUENCE: 1
ggtcgatgta tgtcttgttg                                            20

<210> SEQ ID NO 2
<211> LENGTH: 21
<212> TYPE: DNA
<213> ORGANISM: Primer

```
<400> SEQUENCE: 2
gtctacgtgt gtgctttgta c                                    21

<210> SEQ ID NO 3
<211> LENGTH: 20
<212> TYPE: RNA
<213> ORGANISM: Primer

<400> SEQUENCE: 3
ggucgaugua ugucuuguug                                      20

<210> SEQ ID NO 4
<211> LENGTH: 21
<212> TYPE: RNA
<213> ORGANISM: primer

<400> SEQUENCE: 4
gucuacgugu gugcuuugua c                                    21

<210> SEQ ID NO 5
<211> LENGTH: 21
<212> TYPE: DNA
<213> ORGANISM: oligonucleotide

<400> SEQUENCE: 5
accatggtgc acctgactcc u                                    21

<210> SEQ ID NO 6
<211> LENGTH: 21
<212> TYPE: DNA
<213> ORGANISM: oligonucleotide

<400> SEQUENCE: 6
gaggagaagt ctgccgttac t                                    21

<210> SEQ ID NO 7
<211> LENGTH: 20
<212> TYPE: DNA
<213> ORGANISM: oligonucleotide

<400> SEQUENCE: 7
caggagtcag gtgcaccatg                                      20

<210> SEQ ID NO 8
<211> LENGTH: 21
<212> TYPE: DNA
<213> ORGANISM: oligonucleotide

<400> SEQUENCE: 8
cagtaacggc agacttctcc u                                    21

<210> SEQ ID NO 9
<211> LENGTH: 51
<212> TYPE: DNA
<213> ORGANISM: oligonucleotide

<400> SEQUENCE: 9
gacaccatgg tgcacctgac tccugaggag aagtctgccg ttactgccct g    51
```